United States Patent

Nolley, Jr. et al.

[11] 4,028,069
[45] June 7, 1977

[54] PURIFICATION AND DRYING OF HYDROCARBON STREAMS WITH ADSORBENTS

[75] Inventors: John P. Nolley, Jr., Glendale Heights; John G. Kunesh, Deerfield, both of Ill.

[73] Assignee: UOP Inc., Des Plaines, Ill.

[22] Filed: Aug. 30, 1976

[21] Appl. No.: 719,029

[52] U.S. Cl. .................................. 55/33; 55/62; 55/73

[51] Int. Cl.² ................................ B01D 53/04

[58] Field of Search ............... 55/33, 62, 68, 73, 75

[56] References Cited

UNITED STATES PATENTS

| | | |
|---|---|---|
| 3,455,815 | 7/1969 | Fickel ............................ 55/75 X |
| 3,479,797 | 11/1969 | Spencer et al. .................. 55/62 |
| 3,696,587 | 10/1972 | Young et al. ..................... 55/62 |
| 3,816,975 | 6/1974 | Collins ............................ 55/33 |

*Primary Examiner*—John Adee
*Attorney, Agent, or Firm*—James R. Hoatson, Jr.; Robert W. Erickson; William H. Page, II

[57] ABSTRACT

Contaminants, such as water and hydrogen sulfide, are removed from hydrocarbon streams by the use of beds of solid adsorbents including molecular sieves. The adsorbents are regenerated by heating, with the heating being performed in a closed-loop operation wherein a small quantity of the hydrocarbon being treated is recycled in a closed-loop recirculation system comprising the adsorbent and a heater until the adsorbent reaches an effective regeneration temperature. Closed-loop operation is then terminated, and a regeneration gas is passed into the system and the adsorbent on a once-through basis.

12 Claims, 1 Drawing Figure

U.S. Patent
June 7, 1977
4,028,069
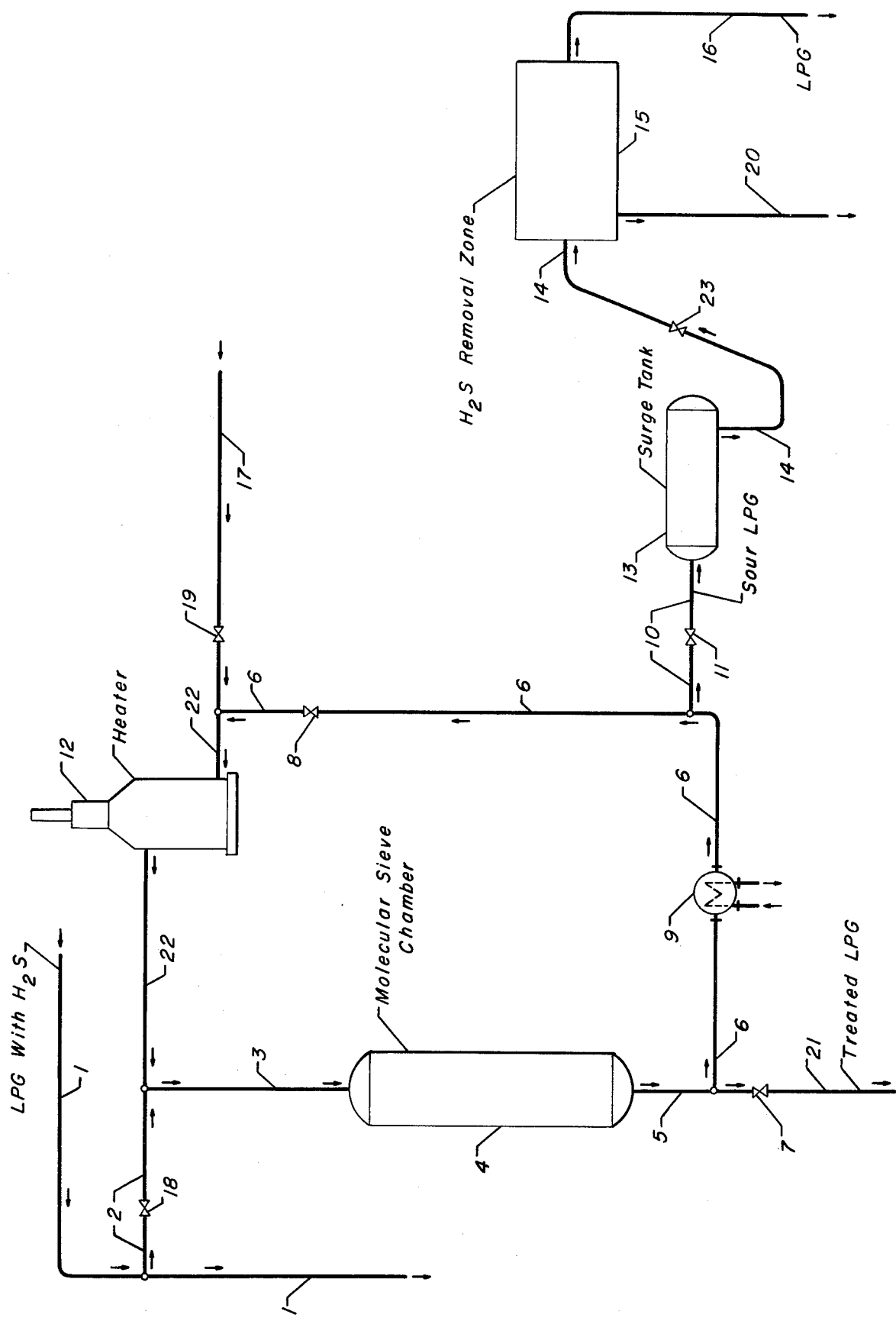

4,028,069

PURIFICATION AND DRYING OF HYDROCARBON STREAMS WITH ADSORBENTS

FIELD OF THE INVENTION

The invention relates to a process for the purification of mineral oils, such as LPG, by the use of a sorption operation. The invention also relates to a method of drying mineral oils, and more particularly to a method of removing hydrogen sulfide from light hydrocarbons by the use of a bed of molecular sieves and then regenerating the molecular sieves by applying heat.

PRIOR ART

The use of beds of solid adsorbents to remove contaminants from both gas and liquid phase hydrocarbon feed streams is highly developed and widely practiced. This is demonstrated by the information on adsorption and ion exchange which forms section 16 of the Fourth Edition of the *Chemical Engineers' Handbook*, McGraw-Hill Book Company, New York, 1963.

Adsorbents are typically used and then regenerated in a repetitive cyclic operation which includes an adsorption period and a regeneration period. Cooling and purge periods may also be employed. Adsorption is performed until the adsorbent material lacks the ability to adequately remove a preselected chemical species from the hydrocarbon feed stream. At this point in time the flow of the feed stream is normally diverted into a second bed of adsorbent material, and the first bed of adsorbent is regenerated. Regeneration is performed by heating the adsorbent to a temperature at which the preselected chemical species is readily released from the adsorbent in a manner hereinafter described. The adsorbent is held at this temperature while a suitable fluid stream, which may be a portion of the treated feed stream, is circulated through the bed of adsorbent to remove the material being released by the adsorbent. When regeneration is complete, the bed of adsorbent is cooled and another adsorption cycle is begun.

Cyclic adsorption and regeneration is described in U.S. Pat. Nos. 2,323,524 (Cl. 34–37), 3,205,163 (Cl. 208–188) and 3,436,839 (Cl. 34–80). These three references teach regeneration cycles wherein a fluid is passed through a heater and the bed of adsorbent, and the effluent of the adsorbent bed is then cooled to effect a condensation and separation of the material being driven off the adsorbent.

Heretofore the standard practice for the regeneration operation has been to gradually raise the temperature of the adsorbent to that needed for regeneration by charging to it a fluid stream which is then either cooled or rejected after it emerges from the adsorbent. The heat which remains in this fluid stream is therefore not utilized. In two of the above references the fluid used to heat and regenerate the adsorbent is recirculated in a closed-loop system which is physically similar to that described herein. However, there are several differences in the method taught by the references and that employed in the subject invention. For instance, in the subject process the effluent of the adsorbent bed is neither cooled nor condensed during the heating period. That is, it is completely recirculated, and it is passed through the heating means several times. Secondly, the recirculation is preferably terminated when the adsorbent reaches a preselected temperature at which the contaminant is readily released, and a regeneration fluid is then passed through the adsorbent on a once-through basis.

SUMMARY OF THE INVENTION

The invention provides an improved method for removing a contaminant from a fluid stream through the use of a fixed bed of adsorbents. A broad embodiment of the invention comprises regenerating the adsorbent by the steps of establishing a closed-loop vapor recirculation system comprising the bed of adsorbent to be regenerated and a heater, and then heating this bed of adsorbent from adsorption conditions to regeneration conditions by continuously recirculating a fixed quantity of a heating fluid through the recirculation system as the temperature of the heating fluid is increased by the operation of the heater.

This method of operation has several advantages. First of all, it reduces the utilities cost of the regeneration operation. This results from the conservation of the heat present in the heating fluid as it emerges from the adsorbent bed at an elevated temperature. By recirculating this effluent it is not necessary to effect its cooling or to heat a stream of fresh heating fluid to this temperature. The savings which result from this are proportional to the frequency of regeneration and to the temperature required for regeneration.

Secondly, the typical and preferred method of heating a bed of adsorbent for the purpose of regeneration calls for a gradual increase in the temperature of the adsorbent. This is accomplished, at least in part, by only gradually increasing the temperature of the heating fluid as it is circulated through the adsorbent. The large size of the adsorbent bed may itself dictate this gradual warming. During this preliminary heating period the adsorbent begins to gradually release some small amount of the previously adsorbed contaminant. The fluid used for the heating operation therefore becomes contaminated with the adsorbate. If this fluid is used on a once-through basis, the result is a large quantity of fluid containing a relatively small amount of contaminant. The invention eliminates this by concentrating the adsorbate in a small quantity of regeneration fluid which is only passed into the adsorbent bed when it has reached the proper regeneration temperature.

The invention also allows utilization of a characteristic rapid increase in the rate of desorption as the regeneration temperature is approached. This increase may be so dramatic that if the concentration of the released contaminant in the effluent of the adsorbent is plotted against regeneration time, the result is a spike or large increase which occurs over a relatively short time period. By the method of the subject invention, no material is withdrawn from the closed-loop recirculation system until this spike or temperature of rapid contaminant release is reached. Open-loop operation is then initiated. Regenerations performed in this manner produce a smaller quantity of used regeneration fluid which has a relatively higher concentration of the adsorbate than prior art methods. This allows economies in the downstream facilities to which the regeneration fluid is eventually discharged. For instance, it is as a general rule more economical to remove a given quantity of a contaminant from a concentrated stream than from a dilute stream. This results from various factors including the smaller size of the downstream equipment needed for such operations as storage, fractionation, incineration, etc.

DETAILED DESCRIPTION

Adsorption is widely practiced in the chemical, petrochemical and petroleum industries for such purposes as removing contaminants from process feed streams, the recovery of valuable chemical compounds, the drying of hydrocarbon streams, the treatment of synthetic or natural gaseous fuels and the removal of environmentally unacceptable materials from effluent streams. For instance solid adsorbents may be used to recover $C_3$–$C_6$ hydrocarbons from a stream of normally gaseous hydrocarbons, such as methane, or to remove carbon dioxide or hydrogen sulfide from a hydrocarbon stream. Adsorbents may be used to effect such operations on both vapor and liquid phase feed streams. The invention is one of general application and can be utilized in any of these applications. The invention may be applied to operations which utilize either physical or chemical adsorption mechanisms to bind the adsorbate.

A 'arge number of differing materials are suitable for use as adsorbents in general, but that employed in any specific process must satisfy several criteria. These include an ability to selectively adsorb the desired chemical compound, a sufficient capacity to justify commercial usage, and sufficient physical strength and thermal stability to withstand the conditions imposed during adsorption and regeneration cycles. Known adsorbents which may be used within the subject process natural materials such as charcoal, activated carbon, and alumina or synthetic materials including silica gel, ion exchange resins, metal oxides and molecular sieves. The selection of the proper adsorbent is within the expertise of those skilled in the art, and guidance is available from standard references and commercial publications. As an example, Type 3A and 4A molecular sieves can be used to adsorb water from hydrocarbons and type 4A can be used to remove $H_2S$ from a stream of normally gaseous hydrocarbons.

Conditions employed during the use of the adsorbent are chosen to promote the effectiveness of the adsorbent and will depend on several varying factors. These include the identity of the chemical compound which it is desired to adsorb, the composition of the fluid in which it is present and the particular adsorbent which is used. In general, adsorption conditions include a temperature of from about 40° F. to 250° F. and a pressure of from atmospheric to about 1200 psig. or higher. Preferably the adsorption operation is carried out at a temperature of 70° F. to 150° F. and a pressure of 10 psig. to 250 psig. With a liquid phase feed stream the pressure should be sufficient to maintain liquid phase conditions at the temperature imposed. The flow rate of the feed stream through the adsorbent may vary widely depending on the concentration of the chemical compound to be removed and the desired useful life of the adsorbent between regenerations. Adsorption operations may be conducted at liquid hourly space velocities ranging from 0.5 to 10.

Regeneration conditions for use with the process described herein preferably include a pressure about equal to or less than that used during the adsorption cycle and a temperature which is at least 200 Fahrenheit degrees higher than that used during adsorption. A general range of regeneration conditions includes a pressure of from atmospheric to about 1200 psig. or higher and a temperature of about 450° F. to 700° F. A preferred temperature range for regeneration is from 450° F. to 650° F. The optimum temperature will depend on the adsorbent and the previously adsorbed chemical compound. Information on regeneration conditions is often available from the manufacturer of the adsorbent. The material recirculated during the closed-loop heating step is preferably a portion of the previously treated feed stream. However, other fluids may be used and may actually be more effective for the regeneration operation. For instance, in the regeneration of metal oxides used to remove $SO_2$ from flue gases the regeneration fluid may be a mixture of hydrogen and nitrogen or some other diluent.

According to the subject method, the used bed of adsorbent is heated to a preselected regeneration temperature by the recirculation of a heating fluid in a closed-loop recirculation system. As the term preselected regeneration temperature is used herein it is intended to indicate the lower of either a temperature 200 Fahrenheit degrees above the temperature previously used during the immediately preceding adsorption operation or the temperature at which the adsorbent's capacity to adsorb the preselected chemical compound is, on a weight basis, less than 20 percent of its capacity at the temperature used in the preceding adsorption operation and an equal pressure. Unless otherwise specified these temperatures refer to average bed temperatures. The term closed-loop recirculation system is intended to refer to an enclosed piping circuit which is capable of recycling a fluid stream through a heater and the bed of the adsorbent several times without the loss or the addition of any fluid. In other words it is a piping system in which the effluent of the adsorbent is passed through a heater and then is once again passed into contact with the adsorbent. This system will also contain a pump or compressor and one or more flow control means used to open the system for passage of a regeneration fluid when the regeneration conditions have been reached and for other purposes.

In accordance with this description, the preferred embodiment of the invention may be characterized as a process for removing $H_2S$ from a feed stream comprising hydrocarbons which comprises the steps of passing the feed stream through a bed of an adsorbent material maintained at adsorption promoting conditions and effecting the transfer of the $H_2S$ from the feed stream to the adsorbent material; regenerating the adsorbent material by the series of steps which comprises terminating passage of the feed stream through the adsorbent material and establishing a closed-loop fluid circulation system comprising the adsorbent material and a heating means and circulating a heating fluid through the circulation system, heating the adsorbent material to a preselected regeneration temperature by adding heat to the heating fluid by use of the heating means, opening the circulation system and removing $H_2S$ from the adsorbent material by charging a regeneration fluid to the circulation system at a point upstream of the adsorbent material and by removing an $H_2S$ rich effluent stream from the circulation system at a point downstream of the adsorbent material; and cooling the adsorbent material to adsorption-promoting conditions and reestablishing the flow of the feed stream through the adsorbent material.

The preferred embodiment of the invention is further illustrated by the drawing. For the purposes of simplicity and clarity of presentation numerous subsystems and assemblies such as controls and pumps have been deleted. To describe the process shown in the drawing it is assumed that a feed stream of liquefied petroleum gases, LPG, containing $C_3$ and $C_4$ hydrocarbons and a minor amount of undesired $H_2S$ is carried through a header system in line 1. When the system illustrated is being operated in an adsorption cycle this stream flows through line 2 into line 3. The feed stream then travels through a bed of 4A molecular sieves at a temperature of about 100° F. and a pressure of about 200 psig. This effects the transfer of the $H_2S$ to the molecular sieves and the production of a treated LPG product stream removed in lines 5 and 21. When the molecular sieves have reached their capacity for $H_2S$ at these conditions, as indicated by the treatment of a measured quantity of the feed stream or by the breakthrough of $H_2S$ in the product stream, a regeneration cycle is begun. This is accomplished by closing valve 18 to direct the flow of the feed stream to another bed of molecular sieves which allows continuous treatment of the feed stream. Valve 7 in line 5 is then closed, and valve 8 in line 6 is opened. This establishes a closed-loop circulation system comprising the adsorbent chamber 4, lines 5, 6, 22 and 3 and a heater 12. Preferably this is a fired heater, but it may utilize hot oil, high pressure steam or electricity to heat the material circulating in line 22.

This closed-loop system contains a quantity of the LPG which has been previously treated. This fixed quantity is recirculated through the system several times by a pump or compressor not shown. As the fluid passes through the heater its temperature is raised, and the temperature of the molecular sieves is therefore increased by contact with this relatively warm stream. The effluent of the adsorbent bed is returned to the heater inlet. During this recirculation valves 19 and 11 are normally closed. Valve 19 may, however, be opened for a short period at the start of the regeneration cycle to provide an additional quantity of regeneration fluid if it is required. If the adsorption operation is performed with a liquid phase feed stream and the regeneration operation is performed with a vapor phase regeneration stream, it will be necessary to drain off liquid and to vent vapor to allow for the expansion caused by vaporization. Once this liquid removal is completed, no further withdrawals should be necessary until the regeneration temperature is reached. The continuous recirculation is continued until the average bed temperature within the sieve chamber reaches the preselected regeneration temperature or above. For this specific operation a temperature of from 550° F. to 650° F. is acceptable for regeneration of the molecular sieves.

At this time open-loop operation is initiated. This is intended to refer to an operation wherein there is a net removal of the adsorbed material, in this case $H_2S$, from the adsorbent chamber through the discharge of an adsorbate-rich stream and the passage of an adsorbate-free stream into the system. This operational mode is achieved by opening valve 19 to pass a stream of regeneration fluid from line 17 through the heater and the adsorbent chamber. This stream comprises a stream of low molecular weight hydrocarbons containing essentially no $H_2S$. It may be a vaporized portion of previously treated LPG or some other readily available stream, such as from a gas concentration unit or reformer, etc. A corresponding effluent stream, which is rich in the $H_2S$ now being released by the molecular sieves, is withdrawn through line 10 by opening valve 11.

During open-loop operation valve 8 is preferably closed. However, it may be only partially closed in order to allow some recycle of regeneration gases through line 6 to provide for a smoother operation and to lessen the temperature differential across the heater. The effluent stream removed in line 10 will contain all of the $H_2S$ driven off the sieves, and it will be more concentrated than a stream of effluent gas which would have been produced if open-loop operation had been conducted during all of the heating period of the regeneration. For instance, if the total closed-loop heating period is 12 hours and the open-loop operation is conducted for only an additional two hours, all of the released $H_2S$ is concentrated in the effluent gas produced in two hours rather than being spread throughout a quantity seven times larger. The gas produced in a 14 hour open-loop operation would have a concentration profile including a period of high $H_2S$ concentration at some higher temperature, and this $H_2S$ rich gas could be segregated from the other gas produced at lower temperatures. However, the remaining gas would be contaminated with $H_2S$, and little if any savings would result from this segregation. Open-loop operation may be terminated after a preset time which has been found adequate or the composition of the effluent stream may be monitored to determine when the adsorbent is no longer releasing appreciable amounts of $H_2S$. The latter mode is preferred since it results in a smaller total quantity of effluent.

The effluent gas in line 10 may be condensed by a means not shown to produce a liquid phase material having a smaller volume more suitable for storage. It is directed into a surge tank 13. The contents of this tank may then be withdrawn at a lower instantaneous rate of flow controlled by valve 23 through line 14 and passed into an $H_2S$ removal zone 15. This zone may be of several different types. For instance, the processes for converting $H_2S$ to elemental sulfur described in U.S. Pat. Nos. 2,972,522; 3,034,865; 3,095,276 and 3,457,046 are suitable for use in this zone. Alternatively an adsorption-stripping operation using caustic or amine solutions can be employed. The sulfur containing effluent stream of this zone may contain either $H_2S$ or elemental sulfur and is removed in line 20. The remaining reclaimed LPG is removed in line 16.

It is normally desirable to cool the newly regenerated adsorbent down to a suitable adsorption temperature prior to restarting the flow of the feed stream through the adsorbent. Preferably, this is also performed in a closed-loop operation. The operation of the heater is terminated. The closed-loop recirculation system is reestablished by closing valve 11 and valve 19 and opening valve 8. Valves 7 and 18 remain closed. A fluid stream, which preferably comprises the last regeneration fluid used in the system or some of the last effluent of the regeneration cycle, is then circulated through the system by a suitable pump or compressor. This fluid stream is cooled by the removal of heat in cooler 9 until the temperature of the fluid stream as it emerges from the adsorbent is at a suitable adsorption temperature. The circulation of this fluid stream is terminated, and valve 8 is then closed. The adsorbent may then be once again placed on-stream by opening valves 7 and 18 to restart the flow of the feed stream.

We claim as our invention:
1. A process for removing a preselected chemical compound from a fluid stream by the use of a bed of a solid adsorbent which comprises the steps of:

a. passing a feed stream comprising a hydrocarbon and a chemical compound different than the hydrocarbon through a first bed of adsorbent material at conditions effective to cause the removal of the chemical compound from the feed stream by adsorption, including a preselected adsorption temperature;

b. switching the passage of the feed stream from through the first bed of adsorbent material to through a second bed of adsorbent material;

c. heating the first bed of adsorbent material by continuously recirculating a fixed quantity of a heating fluid which comprises a hydrocarbon contained in the feed stream through the first bed of adsorbent material in a closed-loop recirculation system comprising a heating means and the first bed of adsorbent material while heat is being added to the heating fluid by the heating means;

d. terminating the closed-loop recirculation of the heating fluid when the first bed of adsorbent material reaches a preselected regeneration temperature;

e. passing a stream of regeneration fluid through the heating means and the first bed of adsorbent material at conditions effective to cause the transfer of the chemical compound from the first bed of adsorbent material to the stream of regeneration fluid and thereby forming a stream rich in the chemical compound and which is removed as an effluent stream; and, f. terminating the removal of the effluent stream when substantially all of the chemical compound has been removed from the first bed of adsorbent material.

2. The process of claim 1 further characterized in that the recirculation system comprises a cooling means and in that after the removal of the effluent stream is terminated the recirculation system is reestablished and a cooling fluid is recirculated therein, and the first bed of adsorbent material is cooled by removing heat from the cooling fluid, the recirculation of the cooling fluid is terminated and the feed stream is again passed through the first bed of adsorbent material.

3. The process of claim 1 further characterized in that the heating fluid comprises a portion of the feed stream.

4. The process of claim 1 further characterized in that the chemical compound is a sulfur compound.

5. The process of claim 1 further characterized in that the chemical compound is carbon dioxide.

6. A process for removing $H_2S$ from a feed stream comprising hydrocarbons which comprises the steps of:
a. passing the feed stream through a bed of an adsorbent material maintained at adsorption promoting conditions and effecting the transfer of the $H_2S$ from the feed stream to the adsorbent material;

b. regenerating the adsorbent material by the series of steps which comprises terminating passage of the feed stream through the adsorbent material and establishing a closed-loop fluid circulation system comprising the adsorbent material and a heating means and circulating a heating fluid through the circulation system, heating the adsorbent material to a preselected regeneration temperature by adding heat to the heating fluid by use of the heating means, opening the circulation system and removing $H_2S$ from the adsorbent material by charging a regeneration fluid to the circulation system at a point upstream of the adsorbent material and by removing an $H_2S$ rich effluent stream from the circulation system at a point downstream of the adsorbent material; and, c. cooling the adsorbent material to adsorption-promoting conditions and reestablishing the flow of the feed stream through the adsorbent material.

7. The process of claim 6 further characterized in that the adsorbent material is cooled by reestablishing the closed-loop fluid circulation system and by circulating a cooling fluid therein, and in that the circulation system comprises a cooling means.

8. The process of claim 6 further characterized in that the feed stream comprises $C_3$ hydrocarbons.

9. A process for drying hydrocarbons which comprises the steps of:
a. passing a feed stream comprising hydrocarbons and water through a bed of a desiccant at conditions which promote the adsorption of water by the desiccant and effecting the drying of the feed stream by the transfer of water from the feed stream to the desiccant;

b. regenerating the desiccant by the series of steps which comprises terminating passage of the feed stream through the desiccant and establishing a closed-loop fluid circulation system comprising the desiccant and a heating means and circulating a heating fluid through the circulation system, heating the desiccant to a preselected regeneration temperature by using the heating means to raise the temperature of the heating fluid, opening the circulation system and removing water from the desiccant by passing a regeneration fluid through the desiccant at conditions which promote the release of water by the desiccant; and, c. cooling the desiccant and reestablishing the flow of the feed stream through the desiccant.

10. The process of claim 9 further characterized in that the feed stream comprises $C_6$ hydrocarbons.

11. The process of claim 9 further characterized in that the feed stream comprises a paraffin having less than six carbon atoms per molecule.

12. The process of claim 9 further characterized in that the circulation system comprises a cooling means and in that the desiccant is cooled by reestablishing the circulation system and by circulating a cooling fluid therein.

* * * * *